United States Patent [19]

Hamajima et al.

[11] Patent Number: 5,720,737
[45] Date of Patent: Feb. 24, 1998

[54] ABSORBENT SHEET, PROCESS FOR PRODUCING THE SAME, AND ABSORBENT ARTICLE

[75] Inventors: Mitsugu Hamajima; Hironori Kawasaki; Yasuhiro Yamamoto; Minoru Nakanishi, all of Tochigi-ken, Japan

[73] Assignee: Kao Corporation, Tokyo, Japan

[21] Appl. No.: 580,248

[22] Filed: Dec. 28, 1995

[30] Foreign Application Priority Data

Dec. 28, 1994 [JP] Japan .................. 6-328860
Dec. 28, 1994 [JP] Japan .................. 6-328861

[51] Int. Cl.⁶ .................. A61F 13/15; A61F 13/20
[52] U.S. Cl. .................. 604/378; 604/366; 604/368; 604/372; 604/374
[58] Field of Search .................. 604/358, 365–366, 604/368, 372, 374, 378

[56] References Cited

U.S. PATENT DOCUMENTS

| | | |
|---|---|---|
| 3,070,095 | 12/1962 | Torr . |
| 3,612,055 | 10/1971 | Mesek et al. .................. 604/378 |
| 3,670,731 | 6/1972 | Harmon . |
| 4,103,062 | 7/1978 | Aberson et al. . |
| 4,186,165 | 1/1980 | Aberson et al. . |
| 4,223,677 | 9/1980 | Anderson .................. 604/378 |
| 4,333,463 | 6/1982 | Holtman . |
| 4,537,590 | 8/1985 | Pieniak et al. . |
| 4,559,050 | 12/1985 | Iskra . |
| 4,596,567 | 6/1986 | Iskra . |
| 4,605,402 | 8/1986 | Iskra . |
| 4,927,582 | 5/1990 | Bryson . |
| 5,021,050 | 6/1991 | Iskra . |
| 5,143,680 | 9/1992 | Molnar et al. . |
| 5,171,391 | 12/1992 | Chmielewski et al. . |
| 5,281,207 | 1/1994 | Chmielewski et al. . |
| 5,330,457 | 7/1994 | Cohen .................. 604/378 |
| 5,350,370 | 9/1994 | Jackson et al. .................. 604/367 |

FOREIGN PATENT DOCUMENTS

| | | |
|---|---|---|
| 0394812 | 10/1990 | European Pat. Off. . |
| 0661030 | 7/1995 | European Pat. Off. . |
| 4-89053 | 3/1992 | Japan . |
| 6-287886 | 10/1994 | Japan . |
| 9110416 | 7/1991 | WIPO . |
| 9214430 | 9/1992 | WIPO . |

*Primary Examiner*—P. Zuttarelli
*Attorney, Agent, or Firm*—Birch, Stewart, Kolasch & Birch, LLP

[57] ABSTRACT

The absorbent sheet according to the present invention is characterized in that:

the absorbent sheet contains bulky cellulose fibers and hydrophilic fine fibers or hydrophilic fine particles; the proportion of the hydrophilic fine fibers or the hydrophilic fine particles is higher in one side of the absorbent sheet than in the other side; the bulky cellulose fibers have an average fiber length of 1 to 20 mm and a degree of fiber roughness of 0.3 mg/m or more; the hydrophilic fine fibers have an average fiber length of 0.02 to 0.5 mm; and the hydrophilic fine particles have an average particle diameter of 0.02 to 0.5 mm. The absorbent sheet is useful as, in particular, an absorbent member of absorbent articles, such as sanitary napkins or disposable articles.

14 Claims, 5 Drawing Sheets

ABSORBENT SHEET, PROCESS FOR PRODUCING THE SAME, AND ABSORBENT ARTICLE

BACKGROUND OF THE INVENTION

This invention relates to an absorbent sheet, a process for producing the same, and an absorbent article containing the same. More particularly, it relates to an absorbent sheet exhibiting excellent performance in liquid absorption, permeation, and diffusion, a process for producing the same, and an absorbent article containing the same.

A number of techniques concerning absorbent articles, such as sanitary napkins and pads for adults suffering from incontinence, have been proposed in order to improve body fluid absorptivity, and improvements have been added to date. Most of the improvements so far made have aimed at increase in rate of liquid absorption, prevention of back-flow from an absorbent member to the surface material, prevention of leakage, and reduction of a sticky feel to the skin.

For example, use of superabsorbent polymers in place of a hydrophilic absorbent sheet or pulp has been proposed. Superabsorbent polymers absorb and retain liquid through a physicochemical action, i.e., ionic osmotic pressure, to show increased liquid absorptivity and also prevents back-flow of absorbed liquid, whereas a hydrophilic absorbent sheet or pulp physically absorbs and retains liquid in the fine spaces thereof. Use of superabsorbent polymers realizes improvement in liquid absorptivity. Nowadays almost all of absorbent articles are provided with an absorbent member containing a superabsorbent polymer in combination with pulp.

However, the absorbent articles using superabsorbent polymers are still unsatisfactory in terms of prevention of leakage as is understood from the fact that the users' primary complaint about these absorbent articles consists in leakage of absorbed liquid.

That is, superabsorbent polymers which absorb and retain liquid through ionic osmotic pressure have a limit in rate of absorption. Further, because superabsorbent polymers would not absorb liquid until they get wet, they had to be used in combination with pulp or an absorbent sheet having a high rate of liquid absorption. However, pulp, when formed into a soft fluff absorbing layer, absorbs liquid only locally and therefore exhibits poor liquid diffusing properties.

In addition, pulp shows compressive recovery and flexural recovery to some extent while dry, but while wet it extremely reduces its strength, scarcely exhibiting these recovery characteristics. Therefore, upon application of a stress, wet pulp undergoes compressive deformation and seriously reduces the space available for liquid absorption (hereinafter referred to as absorbing space). As a result, the liquid once absorbed easily flows back, causing an uncomfortable sticky feel and leaks.

According as the absorbing space is reduced due to deformation, the resistance against liquid permeation to the superabsorbent polymer increases. It follows that the polymer per se is reduced in its absorption efficiency, and the overall rate of reabsorption after deformation is markedly reduced, which often cause leaks.

In order to overcome the poor diffusing properties of fluff pulp and to compensate for the reduction in absorbing space due to compressive deformation, it has been proposed to compress pulp to afford an increased pulp density thereby to improve diffusing properties and back-flow preventive properties. However, these techniques not only fail to solve the essential problem that pulp undergoes extreme reduction in strength upon being wetted, but also turned out to involve such a disadvantage that the resistance against liquid permeation to an absorbent polymer increases greatly due to such a short distance among pulp fibers, resulting in deterioration of absorption efficiency. In other words, an absorbent member consisting of fluff pulp does not satisfy both the requirements of liquid absorption and diffusion and is still insufficient in terms of absorption characteristics and prevention of leakage.

On the other hand, most of the absorbent sheets on the market are those prepared from natural pulp by wet paper making. In a wet paper making process comprising the steps of dehydration, wet pressing, and drying, strong tension is exerted among pulp fibers to make the fibers denser due to the interfacial tension of water and hydrogen bonds in the steps of dehydration and drying. As a result, the resulting absorbent sheet is very slow to absorb and transfer liquid, and has an extremely reduced space for substantial absorption of liquid.

A method for increasing the bulkiness of an absorbent sheet by creping or embossing has been attempted. However, creping or embossing merely brings about an apparent increase in thickness with little increase in liquid absorbing space formed by pulp fibers and no improvement in liquid absorption and permeation properties.

An absorbent sheet mainly comprises bulky cellulose fibers has also been proposed. Because bulky cellulose fibers secure large distance among themselves, an absorbent sheet made up of them is excellent in rate of liquid absorption and rate of liquid permeation but is inferior in liquid diffusing properties. Therefore, the absorbent sheet tends to retain liquid in its surface layer and lacks in a feel of surface dryness. Further, if pressure is imposed on the absorbent sheet having absorbed liquid, back-flow of the absorbed liquid easily occurs. On the other hand, an absorbent sheet consisting mainly of softwood pulp or hardwood pulp having a small fiber diameter has also been proposed. Owing to a capillary action caused by its high density, an absorbent sheet of this type is excellent in liquid absorbing and diffusing properties but inferior in liquid permeation properties so that it retains liquid in the surface thereof and lacks in a feel of surface dryness. Thus, it is difficult for a single absorbent sheet to exhibit liquid absorption, permeation, and diffusion performance.

It has also been attempted to prepare a bulky absorbent sheet by a dry paper making process such as an air lay process, in which pulp fibers are accumulated in a bulky state and bound to each other via an appropriate binder. According to this process, an absorbent sheet having a very low density, a large distance among fibers, and a large liquid absorbing space while dry can be obtained. An absorbent sheet of this type maintains the large liquid absorbing space even on absorbing liquid but scarcely exhibits liquid diffusing properties. It also involves the problem of compressive deformation like fluff pulp when pressure is applied while it is wet.

Nonwoven fabric made of cellulose fibers, such as rayon spun bonded fabric, has also been used as an absorbent sheet. Since nonwoven fabric consists of single fibers, liquid diffusing properties and liquid absorption and permeation properties are conflicting functions in an absorbent sheet made of nonwoven fabric. That is, liquid diffusing properties tend to increase as the diameter of the single fibers is reduced; but a reduction in fiber diameter leads to a reduction in fiber distance, resulting in deterioration of absorption and permeation properties. Conversely, an increase in fiber diameter bring about improvement in absorption and permeation properties but results in deterioration of diffusing properties. Thus, an absorbent sheet comprising nonwoven fabric fails to satisfy both the requirements of liquid diffusion and liquid absorption and permeation.

Japanese Patent Application Laid-Open 4-89053 discloses a highly absorbent and very thin absorbent article using, as an absorbent member, a combination of an absorbent sheet and a superabsorbent polymer which are different from each other in liquid absorption and permeation properties and liquid diffusing properties. This absorbent article assigns individual functions of an absorbent article, i.e., transient absorption, permeation, diffusing, and retention of liquid, to the individual members constituting the absorbent member, i.e., the absorbent sheet and the superabsorbent polymer. Therefore, the absorbent member has a complicated structure, which incurs an increase of cost.

SUMMARY OF THE INVENTION

Accordingly, an object of the present invention is to provide an absorbent sheet which has a large liquid absorbing space and exhibits high liquid absorption and permeation properties and high liquid diffusing properties; and a process for producing the same.

Another object of the present invention is to provide an absorbent article which exhibits high liquid absorption properties, hardly causes leaks, and yet has a very small thickness to give a wearer a comfortable feel on use.

As a result of extensive investigations, the inventors of the present invention have found that an absorbent sheet comprising a specific combination of different fibers with a certain gradient in their proportion possesses both liquid diffusing properties and liquid absorption and permeation properties.

The present invention has been completed based on this finding. The objects of the present invention are accomplished by providing an absorbent sheet containing bulky cellulose fibers and hydrophilic fine fibers or hydrophilic fine particles, which is characterized in that:

the proportion of the hydrophilic fine fibers or the hydrophilic fine particles is higher in one side of the absorbent sheet than in the other side;

the bulky cellulose fibers have an average fiber length of 1 to 20 mm and a degree of fiber roughness of 0.3 mg/m or more;

the hydrophilic fine fibers have an average fiber length of 0.02 to 0.5 mm; and the hydrophilic fine particles have an average particle diameter of 0.02 to 0.5 mm.

The present invention further provides a process for producing an absorbent sheet comprising the steps of:

forming a slurry by dispersing bulky cellulose fibers having an average fiber length of 1 to 20 mm and hydrophilic fine fibers having an average fiber length of 0.02 to 0.5 mm or hydrophilic fine particles having an average particle diameter of 0.02 to 0.5 mm in water;

spreading the slurry on a paper forming wire to form a paper layer on the wire; and dehydrating and drying the paper layer.

The present invention furthermore provides an absorbent article comprising a liquid permeable topsheet, a liquid impermeable backsheet, and a liquid retentive absorbent member interposed between the topsheet and the backsheet, which is characterized in that:

the absorbent member contains an absorbent sheet and a superabsorbent polymer;

the absorbent sheet contains bulky cellulose fibers and hydrophilic fine fibers or hydrophilic fine particles;

the proportion of the hydrophilic fine fibers or hydrophilic fine particles is higher in one side of the absorbent sheet than in the other side;

the bulky cellulose fibers have an average fiber length of 1 to 20 mm;

the hydrophilic fine fibers having an average fiber length of 0.02 to 0.5 mm; and the hydrophilic fine particles have an average fiber diameter of 0.02 to 0.5 mm.

The absorbent sheet of the present invention is useful as pads for postpartum care, nursing breast pads, underwear pads, pads for absorbing sweat, absorbent turbans for perming, drip sheets, medical pads, undersheets for a bed, and the like and is particularly useful as an absorbent member of absorbent articles, such as sanitary napkins and disposable diapers.

The absorbent articles of the present invention are useful as sanitary napkins, disposable diapers, hygienic pads, medical pads, pads for incontinence, nursing breast pads, and the like, especially as sanitary napkins and disposable diapers.

The absorbent sheet of the present invention contains bulky cellulose fibers and hydrophilic fine fibers or hydrophilic fine particles. The bulky cellulose fibers form a bulky network structure in the absorbent sheet. The proportion of the hydrophilic fine fibers or particles is higher in one side of the absorbent sheet than in the other side. As a result, the side of the absorbent sheet having a lower proportion of the hydrophilic fine fibers or particles exhibits a high rate of liquid absorption, excellent local liquid absorptivity, and excellent liquid permeation properties. On the other hand, the side having a higher proportion of the hydrophilic fine fibers or particles exhibits excellent liquid diffusing properties because of the high surface area of the fine fibers or particles. Therefore, the liquid having passed through the side with a lower proportion of the hydrophilic fine fibers or particles quickly diffuses over the other side. In other words, the absorbent sheet of the present invention, while having a single structure, combines both the function of liquid absorption and permeation and the function of liquid diffusion. Since the absorbent sheet of the present invention thus has a gradient in liquid absorption and diffusion in its single structure, it has a high rate of liquid absorption, excellent local liquid absorptivity, and excellent liquid permeation and diffusing properties, thereby to give a wearer a good feel of dryness.

According to the process of the present invention for producing an absorbent sheet, a non-uniform distribution of the hydrophilic fine fibers or particles can be easily provided in the thickness direction by taking advantage of the difference in fiber length or diameter between the bulky cellulose fibers and the hydrophilic fine fibers or particles, thereby to produce the above-described absorbent sheet through a single process with ease.

The absorbent article comprising the absorbent sheet of the present invention realizes an ideal flow of liquid from the liquid permeable topsheet to the superabsorbent polymer present in the liquid retentive absorbent member owing to the above-mentioned functions. Accordingly, the absorbent article of the present invention is highly absorbent, causes few leaks, and can be designed to be so ultrathin as to give a comfortable feel on use.

DETAILED DESCRIPTION OF THE INVENTION

Figure 1:
FIG. 1 is a schematic view illustrating the cross section of the absorbent sheet of the present invention in its thickness direction.

The absorbent sheet according to the present invention and a preferred process for producing the same will be described in detail by referring to the accompanying drawings. FIG. 1 is a schematic cross section of the absorbent sheet of the present invention in its thickness direction, and FIG. 2 is a schematic view showing the condition of liquid absorption and diffusion in the absorbent sheet of the present invention.

As shown in FIG. 1, the absorbent sheet 11 of the present invention contains bulky cellulose fibers 12 and hydrophilic fine fibers 13 or hydrophilic fine particles 13 and is characterized in that the proportion of the hydrophilic fine fibers or particles 13 is higher in one side of the absorbent sheet than in the other side; the bulky cellulose fibers 12 have an average fiber length of 1 to 20 mm and a degree of fiber roughness of 0.3 mg/m or more; the hydrophilic fine fibers 13 have an average fiber length of 0.02 to 0.5 mm; and hydrophilic fine particles 13 have an average particle diameter of 0.02 to 0.5 mm.

As shown in FIG. 1, the hydrophilic fine fibers or particles 13 contained in the absorbent sheet 11 have a distribution gradient in the thickness direction. That is, the proportion of the hydrophilic fine fibers or particles 13 is higher in one of the sides of the absorbent sheet 11 than in the other side. In what follows, the side having a lower proportion of the hydrophilic fine fibers or particles 13 will be referred to as a "surface side", while the other side having a higher proportion of the hydrophilic fine fibers or particles as a "back side".

Figure 2:
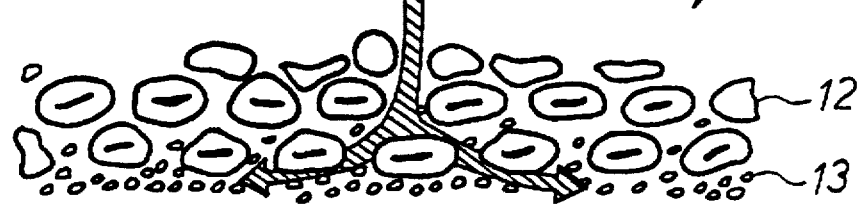
FIG. 2 is a schematic view illustrating the condition of liquid absorption and diffusion in the absorbent sheet of the present invention.

As shown in FIG. 2, the surface side and its vicinities of the absorbent sheet 11 predominantly comprises the bulky cellulose fibers 12 and therefore perform a function of rapidly absorbing liquid and letting the liquid quickly permeate to the back side, as indicated by the arrow. In other words, this area serves primarily for the function as a liquid absorbent and permeable layer. On the other hand, the back side and its vicinities predominantly comprises the hydrophilic fine fibers or particles 13 and therefore perform a function of quickly diffusing the liquid having permeated from the surface side. In other words, this area serves primarily for the function as a diffusing layer. The absorbent sheet 11 is thus characterized by having an absorbent and permeable layer and a diffusing layer in its single structure, thereby exhibiting high liquid absorbing properties and keeps a feel of surface dryness even after liquid absorption.

There is a great difference in liquid diffusing properties between the surface side and the back side. Liquid is quickly diffused in the back side (i.e., diffusing layer) predominantly comprising the hydrophilic fine fibers or particles, while liquid is quickly absorbed and transferred but is not so rapidly diffused in the surface side (i.e., absorbent and permeable layer) predominantly comprising the bulky cellulose fibers. In other words, the absorbent sheet of the present invention shows a gradient in liquid diffusion in its thickness direction. Taking the diffusion area of 1 g of physiological saline as a measure for liquid diffusing properties, the diffusion area in the back side is larger than in the surface side. A ratio of the diffusion area in the back side to that in the surface side is preferably 1.2 or higher, more preferably 1.5 to 20, still preferably 2 to 20. The details for the measurement of diffusion area will be described later.

The increase of the proportion of the hydrophilic fine fibers or particles from the surface side to the back side may be either continuous or discontinuous (in steps) at a certain depth.

The bulky cellulose fibers may be uniformly distributed in the thickness direction of the absorbent sheet, but is preferably present in the surface side in a higher proportion than in the back side. That is, the proportion of the bulky cellulose fibers preferably has a gradient in the thickness direction. The increase of the proportion of the bulky cellulose fibers from the surface to back sides may be either continuous or in steps at a certain depth.

In greater detail, in a preferred mode of gradient, about 5 to 70% by weight, still preferably about 10 to 50% by weight, of the total hydrophilic fine fibers or particles be present in the area from the back side to about ⅓ the thickness of the absorbent sheet to form the above-mentioned diffusing layer predominantly comprising the hydrophilic fine fibers or particles.

It is preferable, on the other hand, that about 60 to 100% by weight, still preferably about 70 to 97% by weight, of the total bulky cellulose fibers be present in the area from the surface side to about ⅔ the thickness of the absorbent sheet to form the above-mentioned absorbent and permeable layer predominantly comprising the bulky cellulose fibers.

The distribution of the bulky cellulose fibers and the hydrophilic fine fibers or particles in the thickness direction of the absorbent sheet may be varied either continuously or stepwise at a certain depth as stated above. In the above-described preferred mode of distribution gradient of the bulky cellulose fibers and the hydrophilic fine fibers or particles, the liquid absorption and permeation properties and diffusing properties are exerted more appreciably.

As mentioned above, the absorbent sheet of the present invention exhibits liquid absorption and permeation properties primarily in the surface side thereof and liquid diffusing properties primarily in the back side thereof. Accordingly, it is preferable that the absorbent sheet be used with its surface side facing to the side first to absorb liquid.

The proportions of the bulky cellulose fibers and the hydrophilic fine fibers or particles in the absorbent sheet are not particularly limited. The bulky cellulose fibers are preferably present in an amount of 50 to 97 parts by weight, still preferably 70 to 95 parts by weight, based on 100 parts by weight of the absorbent sheet. If the proportion of the bulky cellulose fibers is less than 50 parts by weight, the resulting sheet has insufficient bulkiness in its network structure and tends to fail to combine a permeation function and a diffusing function. If the proportion exceeds 97 parts by weight, the proportion of the hydrophilic fine fibers or particles is low for obtaining sufficient diffusing properties. Accordingly, the proportion of the bulky cellulose fibers preferably falls within the above range.

The hydrophilic fine fibers or particles are preferably present in an amount of 3 to 50 parts by weight, still preferably 5 to 30 parts by weight, based on 100 parts by weight of the absorbent sheet. If the proportion of the hydrophilic fine fibers or particles is less than 3 parts by weight, the absorbent sheet tends to have insufficient diffusing properties. If it exceeds 50 parts by weight, the proportion of the hydrophilic fine fibers or particles in the surface side of the absorbent sheet becomes large only to have insufficient liquid permeability. Accordingly, the proportion of the hydrophilic fine fibers or particles preferably falls within the above range.

If desired, the absorbent sheet of the present invention may contain thermally fusible bonding fibers which melt and adhere to each other on being heated. Incorporation of thermally fusible bonding fibers is effective to maintain the structural stability while wet.

The thermally fusible bonding fibers are preferably added in an amount of 2 to 30 parts by weight, still preferably 3 to 20 parts by weight, based on 100 parts by weight of the absorbent sheet. If the amount is less than 2 parts by weight, the resulting absorbent sheet tends to have insufficient strength after absorbing liquid, or the mixed state of the bulky cellulose fibers and the hydrophilic fine fibers or particles in the absorbent sheet may be changed, sometimes resulting in the failure of maintaining the diffusion gradient. If the amount of the thermally fusible bonding fibers exceeds 30 parts by weight, the absorbent sheet reduces its hydrophilic properties as a whole and tends to have insufficient rate of liquid absorption or insufficient diffusing performance. Accordingly, the proportion of the thermally fusible bonding fibers preferably falls within the above range.

Other components which may be arbitrarily added to the absorbent sheet of the present invention include other kinds of pulp, such as softwood pulp, hardwood pulp, and straw pulp; and, as strengthening assistant, dialdehyde starch, sponge, and carboxymethyl cellulose. These components may be added in an amount of 0 to 20 parts by weight based on 100 parts by weight of the absorbent sheet.

While not limiting, the basis weight of the absorbent sheet of the present invention is preferably 10 to 200 g/m$^2$, still preferably 20 to 150 g/m$^2$. An absorbent sheet having a basis weight of less than 10 g/m$^2$ is too thin, tending to fail to exert both the permeation and diffusion functions. An absorbent sheet having a basis weight exceeding 200 g/m$^2$ is too thick, tending to fail to smoothly transfer liquid through permeation and diffusion. Accordingly, the above range is preferred.

While not limiting, the thickness of the absorbent sheet preferably ranges from 0.2 to 2 mm, still preferably 0.2 to 1 mm, under an applied load of 2.5 g/m$^2$. An absorbent sheet thinner than 0.2 mm tends to fail to serve for the permeation and diffusion functions because the absorbent sheet is too thin. If the thickness exceeds 2 mm, it tends to be difficult to transfer liquid smoothly through permeation and diffusion. Accordingly, the thickness of the absorbent sheet preferably falls within the above range.

In a preferred embodiment, the absorbent sheet comprises 50 to 97 parts by weight of the bulky cellulose fibers and 3 to 50 parts by weight of the hydrophilic fine fibers or particles, based on 100 parts by weight of the absorbent sheet.

In a still preferred embodiment, the absorbent sheet comprises 70 to 95 parts by weight of the bulky cellulose fibers, 5 to 30 parts by weight of the hydrophilic fine fibers or particles, and 2 to 30 parts by weight of the thermally fusible bonding fibers, based on 100 parts by weight of the absorbent sheet, and the basis weight of the absorbent sheet is 10 to 200 g/m$^2$.

Figure 3:
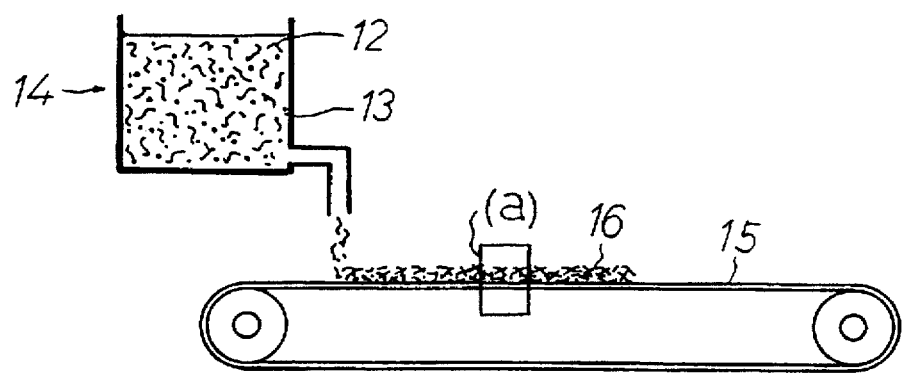
FIG. 3 is a schematic view illustrating a preferred process for producing the absorbent sheet of the present invention.

The absorbent sheet of the present invention is preferably produced according to a process shown in FIG. 3, which comprises the steps of:

forming a slurry 14 by dispersing the bulky cellulose fibers 12 having an average fiber length of 1 to 20 mm and the hydrophilic fine fibers 13 having an average fiber length of 0.02 to 0.5 mm or hydrophilic fine particles 13 having an average particle diameter of 0.02 to 0.5 mm in water;

spreading the slurry 14 on a paper forming wire 15 to form a paper layer 16 on the paper forming wire 15; and dehydrating and drying the paper layer 16.

As stated above, the absorbent sheet of the present invention is preferably produced by a wet paper making process. Paper making machines to be used are not particularly limited and include, for example, a cylinder paper making machine, a former paper making machine, and a wire paper making machine.

Figure 4:
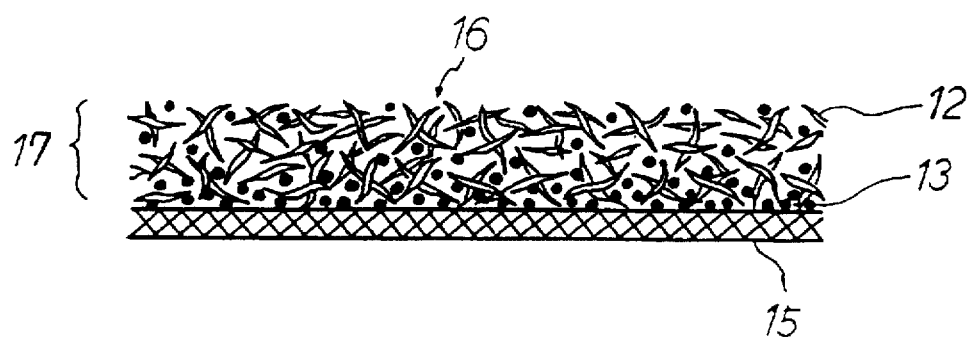
FIG. 4 is an enlarged view of part (a) of FIG.

The above-mentioned paper making process is explained below with reference to FIG. 4, an enlarged view of part (a) of FIG. 3.

When the slurry 14 is spread over the wire 15, water in the slurry 14 is drained through the wire 15 to form the paper layer 16 on the wire 15. In the paper layer 16, the bulky cellulose fibers 12 form a bulky network structure 17 over the entire thickness as shown in FIG. 4. Finer than the bulky cellulose fibers 12, the hydrophilic fine fibers or particles 13 in the slurry 14 pass through the network structure 17 together with water and are accumulated on the wire 15. As a result, the hydrophilic fine fibers or particles 13 are distributed with a gradient in the thickness direction of the absorbent sheet 11. That is, as shown in FIG. 4, the proportion of the hydrophilic fine fibers or particles 13 is higher in the side in contact with the wire 15 than in the other side.

In the preferred process for producing the absorbent sheet of the present invention, the proportion of the hydrophilic fine fibers or particles 13 is provided with a gradient in the thickness direction of the absorbent sheet, making use of the difference in fiber length or diameter between the bulky cellulose fibers 12 and the hydrophilic fine fibers or particles 13.

The concentration of the bulky cellulose fibers 12 in the slurry is preferably 0.02 to 1% by weight, still preferably 0.03 to 0.7% by weight. If the concentration of the bulky cellulose fibers is less than 0.02% by weight, the resulting absorbent sheet tends to have insufficient rate of liquid permeation, or the amount of drain would be so increased for reaching a desired basis weight, which leads to an energy loss. If the concentration of the bulky cellulose fibers 12 is higher than 1% by weight, the diffusibility of the fibers is deteriorated, tending to result in unevenness of the paper layer. Accordingly, the above-mentioned range of concentration is preferred.

The concentration of the hydrophilic fine fibers or particles 13 in the slurry is preferably 0.002 to 0.5% by weight, still preferably 0.003 to 0.3% by weight. If the concentration is less than 0.002% by weight, the resulting absorbent sheet tends to fail to have sufficient diffusing properties as desired. If it exceeds 0.5% by weight, the hydrophilic fine fibers or particles 13 tend to appear also in the surface side in an appreciable amount so that a desired diffusion gradient may not be obtained. Accordingly, the above concentration range is desirable.

The thermally fusible bonding fibers which are arbitrarily used in the absorbent sheet are preferably used in the slurry at a concentration of 0.001 to 0.3% by weight, still preferably 0.002 to 0.2% by weight. If the concentration is less than 0.001% by weight, the purpose of stably maintaining the structure of the absorbent sheet may not be achieved in some cases. If the concentration exceeds 0.3% by weight, the hydrophilic properties of the absorbent sheet tends to be impaired as a whole. Accordingly, the above concentration range is preferred.

As mentioned above, according to the preferred process for preparing the absorbent sheet of the present invention, the slurry 14 spread over the wire 15 forms a bulky network structure 17 comprising the bulky cellulose fibers 12, and the hydrophilic fine fibers or particles 13 pass through the bulky network structure 17 and are accumulated on the wire 15. To this effect, it is important that the average fiber length of the hydrophilic fine fibers 13 or the average particle diameter of hydrophilic fine particles 13 be greater than the mesh size of the wire 15. Otherwise, the hydrophilic fine fibers or particles 13 would pass through the openings of the wire 15, unfavorably failing to effectively provide a distribution gradient of the hydrophilic fine fibers or particles 13 in the thickness direction. If the mesh size of the wire 15 is too small, the hydrophilic fine fibers or particles 13 clog the openings of the wire 15. Accordingly, the mesh size (opening size) of the wire 15 is preferably 22 to 300 μm (corresponding to 580 to 50 mesh), still preferably 45 to 250 μm (corresponding to 330 to 60 mesh) (the mesh is as measured according to new JIS (Japanese Industrial Standard) (1987)).

According to the preferred process for preparing the absorbent sheet, a distribution gradient of the hydrophilic fine fibers or particles 13 can be provided in the thickness direction with ease. The degree of the gradient depends on the rate of dehydration (drainage rate) of the paper layer 16 formed on the wire 15. While varying depending on the paper making speed and the basis weight of the absorbent sheet, the gradient becomes smaller as the rate of dehydration decreases, ultimately distributing fine fibers or particles 13 substantially uniformly in the thickness direction of the absorbent sheet. Although a high rate of dehydration is favorable for making the gradient steeper, high energy is required for increasing the rate of dehydration. From these considerations, a preferred rate of dehydration is 2 ml/(cm²·sec) or more, still preferably 3 to 30 ml/(cm²·sec). Dehydration can be conducted by means of a suction box as is used in common wet paper making machines.

The above-described process saves a lot of labor because an absorbent sheet combining a liquid absorption and permeation function and a liquid diffusing function can be produced through a single paper making process.

While the process for producing the absorbent sheet has been described referring to the preferred embodiments thereof, the process which can be used for the production of the absorbent sheet of the present invention is by no means limited thereto, and include, for example, a dry paper making process.

An alternative process for producing the absorbent sheet of the present invention comprises previously forming a fiber web comprising the bulky cellulose fibers, spreading the hydrophilic fine fibers or particles on the fiber web, followed by drying to form the laminate into a unitary body to obtain an absorbent sheet having a layer of the bulky cellulose fibers on one side and a layer predominantly comprising the hydrophilic fine fibers or particles on the other side. According to this process, there is provided an absorbent sheet in which the proportions of the bulky cellulose fibers and the hydrophilic fine fibers or particles vary stepwise in the thickness direction.

The bulky cellulose fibers which can be used in the absorbent sheet of the present invention are described below in detail.

It is desirable for the bulky cellulose fibers to form a network structure. Such a network structure is a preferred structure in order for liquid to be rapidly absorbed and transferred to the back side. For this purpose, bulky cellulose fibers 13 should have an average fiber length of 1 to 20 mm, and preferably of 2 to 10 mm, still preferably 2 to 5 mm. If the average fiber length is less than 1 mm, a bulky network structure cannot be formed. Besides, the hydrophilic fine fibers or particles could not pass through the network structure. If the average fiber length is longer than 20 mm, the fibers have poor dispersibility in water, failing to provide a uniform network structure.

Any kind of cellulose fibers can be used as the bulky cellulose fibers as far as they are bulky. For example, natural cellulose, such as wood pulp and cotton; and regenerated cellulose, such as rayon and cuprammonium rayon, can be used. From an economical standpoint, wood pulp is preferred. Softwood kraft pulp is particularly preferred. These cellulose fibers may be used either individually or as a mixture of two or more thereof.

A preferred example of the bulky cellulose fibers is crosslinked cellulose fibers obtained by intramolecular and/or intermolecular crosslinking of cellulose fibers. Crosslinked cellulose fibers are preferred for capability of maintaining a bulky structure even while wet. A more preferred example of the bulky cellulose fibers is crosslinked pulp fibers, and still preferred example of the bulky cellulose fibers is crosslinked cellulose fibers obtained by crosslinking pulp fibers having an average fiber length of 2 to 5 mm.

While not particularly limiting, crosslinking of cellulose fibers can be carried out by using a crosslinking agent. Useful crosslinking agents include N-methylol compounds, such as dimethylolethyleneurea and dimethyloldihydroxyethyleneurea; polycarboxylic acids, such as citric acid, tricarballylic acid, and butanetetracarboxylic acid; polyols, such as dimethylhydroxyethyleneurea; and polyglycidyl ether compounds. Polycarboxylic acids or polyglycidyl ether compounds which do not generate formalin harmful to human bodies on crosslinking are preferred.

The crosslinking agent is preferably used in an amount of 0.2 to 20 parts by weight, based on 100 parts by weight of cellulose fibers. If the amount of the crosslinking agent is less than 0.2 part by weight, the resulting crosslinked cellulose fibers have an insufficient degree of crosslinking and tend to undergo great reduction in modulus of elasticity while wet. At amounts exceeding 20 parts by weight, the crosslinked fibers are too stiff and brittle under a stress applied. Accordingly, the amount of the crosslinking agent to be used preferably falls within the above range.

Crosslinking of cellulose fibers using the above-mentioned crosslinking agent can be carried out by, for example, immersing cellulose fibers in an aqueous solution of the crosslinking agent containing, if desired, a catalyst, dehydrating the impregnated cellulose fibers to have a prescribed add-on of the crosslinking agent aqueous solution, and heating the fibers to a crosslinking temperature; or spraying the crosslinking agent aqueous solution onto the cellulose fibers to give a prescribed add-on, followed by heating to induce crosslinking.

Also, the bulky cellulose fibers have a degree of fiber roughness of 0.3 mg/m or more as well as the average fiber length of 1 to 20 mm. Such cellulose fibers are accumulated in a bulky state to easily form a bulky network structure.

The term "degree of fiber roughness" as used herein means a measure indicative of fineness of fibers having non-uniform fineness. The degree of fiber roughness can be measured, for example, with a fiber roughness meter "FS-200" manufactured by Kajaani Electronics, LTD.

As stated above, the bulky cellulose fibers to be used have a degree of fiber roughness of 0.3 mg/m or more, preferably 0.3 to 2 mg/m, more preferably 0.32 to 1 mg/m.

Specific examples of the cellulose fibers having a degree of fiber roughness of 0.3 mg/m or more include softwood kraft pulp "Albacel" produced by Federal Paper Board Co. and "Indorayon" produced by PT Inti Indorayon Utama.

Besides having the above-mentioned average fiber length and the degree of fiber roughness, the bulky cellulose fibers preferably have a degree of fiber roundness of 0.5 to 1 in the fiber cross section. Cellulose fibers having a degree of fiber roundness in the fiber cross section of 0.5 to 1 is preferred because of low resistance against liquid transfer to afford an increased rate of liquid permeation. It is still preferred that the degree of fiber roundness in the fiber cross section is 0.55 to 1. The method of measuring a degree of fiber roundness in the fiber cross section will be described later.

While wood pulp is preferably used as cellulose fibers as previously mentioned, wood pulp generally has a flat section owing to delignination treatment and mostly has a degree of fiber roundness in the fiber cross section of less than 0.5. The degree of fiber roundness in the fiber cross section of such wood pulp can be increased to 0.5 or more by, for example, mercerizing wood pulp fibers having an average fiber length of 1 to 20 mm and a degree of fiber roughness of 0.3 mg/m or more to expand the cross section of wood pulp fibers.

Thus, cellulose fibers having a degree of fiber roundness in the fiber cross section of 0.5 to 1 preferably include mercerized pulp having a degree of the fiber roundness in the fiber cross section of 0.5 to 1. Specific examples of commercially available mercerized pulp which can be used in the present invention include "Filtranier" and "Porosanier" both produced by ITT Rayonier Inc.

Crosslinked mercerized pulp obtained by crosslinking the above-mentioned mercerized pulp is also preferably used in the present invention.

According to the present invention, cellulose fibers (pulp) having an average fiber length of 2 to 5 mm, a degree of fiber roughness of 0.3 mg/m or more, and a degree of fiber roundness in the fiber cross section of 0.5 to 1 are also preferred.

Still preferred bulky cellulose fibers are those obtained by crosslinking pulp having an average fiber length of 2 to 5 mm, a degree of fiber roughness of 0.3 mg/m or more and a degree of fiber roundness in the fiber cross section of 0.5 to 1 according to the above-mentioned crosslinking methods.

Particularly preferred bulky cellulose fibers are those obtained by mercerizing pulp having an average fiber length of 2 to 5 mm and a degree of fiber roughness of 0.3 mg/m or more to adjust the degree of fiber roundness in the fiber cross section to 0.5 to 1 and then crosslinking the mercerized pulp according to the above-described crosslinking methods.

The hydrophilic fine fibers have a hydrophilic surface and an average fiber length of 0.02 to 0.5 mm, preferably 0.03 to 0.3 mm. The hydrophilic fine particles have a hydrophilic surface and an average particle diameter of 0.02 to 0.5 mm, preferably 0.03 to 0.3 mm. If the average fiber length or average particle diameter is less than 0.02 mm, such fine fibers or particles would pass through a paper making wire and cannot be accumulated on the wire when the absorbent sheet is prepared by the above-described preferred process. If the average fiber length or average particle diameter exceeds 0.5 mm, such fibers or particles cannot pass through the network structure made up of the bulky cellulose fibers and cannot be accumulated on the wire in the preferred process.

As far as the above requirements are met, the hydrophilic fine fibers or particles are not particularly limited. For example, suitable hydrophilic fine fibers or particles include those made of cellulose fibers, such as pulp, cotton, and rayon; those made of hydrophilic synthetic fibers, such as polyacrylonitrile fiber and polyvinyl alcohol fiber; and inorganic fibers or particles, such as kaolin, bentonite, and hydrotalcite. These hydrophilic fine fibers or particles may be used either individually or as a mixture of two or more thereof. A mixture of the hydrophilic fine fibers and the hydrophilic fine particles may also be used.

Commercially available hydrophilic fine fibers and hydrophilic fine particles can be made use of. Among useful commercial products is "Pulp Flock", a product of Sanyo-Kokusaku Pulp Co., Ltd., which is prepared by beating wood pulp, such as softwood pulp or hardwood pulp, mechanically grinding the beaten pulp, followed by classifying using a sieve having 0.5 mm or smaller openings. Also included are fine cellulose fibers or particles obtained by mechanically grinding cellulose fibers, such as wood pulp, hydrolyzing with an acid, and further mechanically grinding (e.g., "KC Flock" produced by Sanyo-Kokusaku Pulp Co., Ltd. and "Avicel" produced by Asahi Chemical Industry Co., Ltd.). Commercially available inorganic fine fibers include water-containing magnesium silicate fibers (e.g., "Eight Plus ML-30" produced by Mizusawa Kagaku Kogyo K.K.). Of these commercial products, fine cellulose fibers or particles obtained by finely grinding pulp are preferred for their inexpensiveness.

The thermally fusible bonding fibers which are arbitrarily used in the absorbent sheet of the present invention are explained below.

Examples of the thermally fusible bonding fibers include polyolefin fibers, such as polyethylene, polypropylene, and polyvinyl alcohol, polyester fibers, polyethylene-polypropylene conjugate fibers, polyethylene-polyester conjugate fibers, low-melting polyester-polyester conjugate fibers, polyvinyl alcohol-polypropylene conjugate fibers having a hydrophilic surface, and polyvinyl alcohol-polyester conjugate fibers. The conjugate fibers may be either of a core/sheath type or a side-by-side type. These thermally fusible bonding fibers may be used either individually or as a mixture of two or more thereof. Polyvinyl alcohol fibers and polyester fibers are preferred for use in the present invention.

The thermally fusible bonding fibers preferably have an average fiber length of 2 to 60 mm, still preferably 3 to 20 mm. If the average fiber length is less than 2 mm, the strengthening effect produced tends to be insufficient. If it exceeds 60 mm, the fibers cannot be uniformly dispersed in water, giving uneven strength. Therefore, the above range is preferred. Further, the thermally fusible bonding fibers preferably have a fiber diameter of 0.1 to 3 denier, still preferably 0.5 to 2 denier. If the fiber diameter is less than 0.1 denier, the strengthening effect tends to be insufficient for giving strength to the absorbent sheet as a whole. If the fiber diameter exceeds 3 deniers, the number of fiber bonds is reduced to make the strengthening effect insufficient. Therefore, the above range is preferred.

The absorbent article according to the present invention will now be explained by referring to FIGS. 5 and 6.

Figure 5:
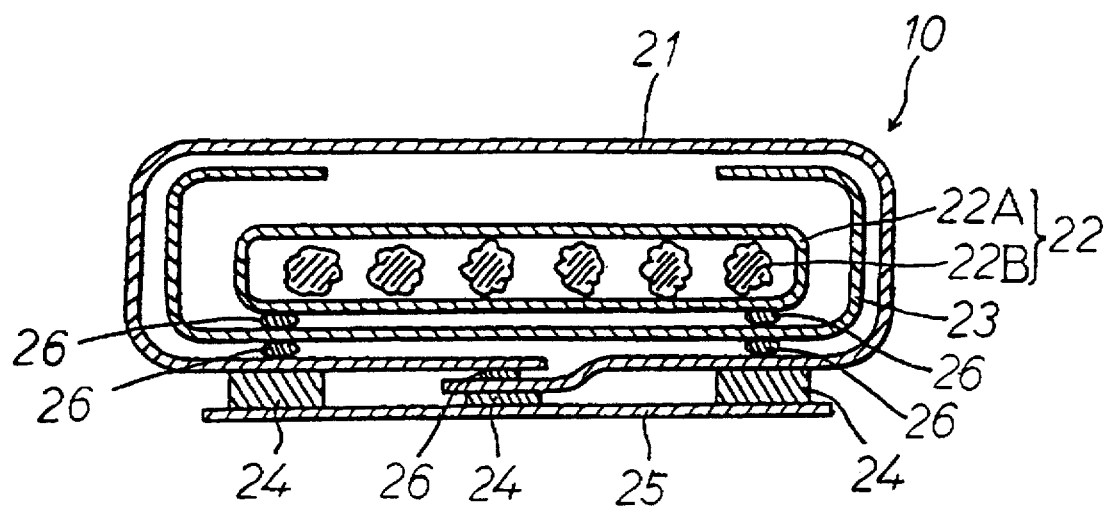
FIG. 5 is a schematic view illustrating the transverse section of a sanitary napkin as one embodiment of the absorbent article of the present invention.

FIG. 5 is a schematic transverse section of a sanitary napkin as an embodiment of the absorbent article according to the present invention. FIG. 6 is a schematic transverse section of a sanitary napkin as another embodiment, the figure corresponding to FIG. 5.

The sanitary napkin 10 shown in FIG. 5 comprises a liquid permeable topsheet 21, a liquid impermeable backsheet 23, and a liquid retentive absorbent member 22 interposed between the topsheet 21 and the backsheet 23.

In detail, the sanitary napkin 10 practically has a rectangular shape. When it is worn, it is applied to the body with the topsheet 21 in contact with the skin, and the backsheet 23 with underwear. The absorbent member 22 is interposed between the topsheet 21 and the backsheet 23.

As shown in FIG. 5, the bottom, all the sides, and the peripheral portion of the upper surface of the absorbent member 22 are covered with the backsheet 23. All the surfaces of the combination of the absorbent member 22 and the backsheet 23 are covered with the topsheet 21. Accordingly, the central area of the upper surface of the absorbent member 22 is covered directly with the topsheet 21. Therefore, liquid permeates through the topsheet 21 directly into the absorbent member 22.

On the side to be brought into contact with underwear are provided three adhesive bands 24 along the longitudinal direction. The adhesive bands 24 are protected by a release paper 25 before use. In FIG. 5, reference numeral 26 indicates adhesive by which the absorbent member 22 and the backsheet 23 are bonded together.

The topsheet 21 is not particularly limited as long as it allows liquid to permeate into the absorbent member 22. Materials having an underwear-like touch are preferred. Such materials include thermoplastic woven cloth, nonwoven cloth and porous films. Perforated films consisting of polyolefins, such as low-density polyethylene, are particularly preferred.

Figure 7A:
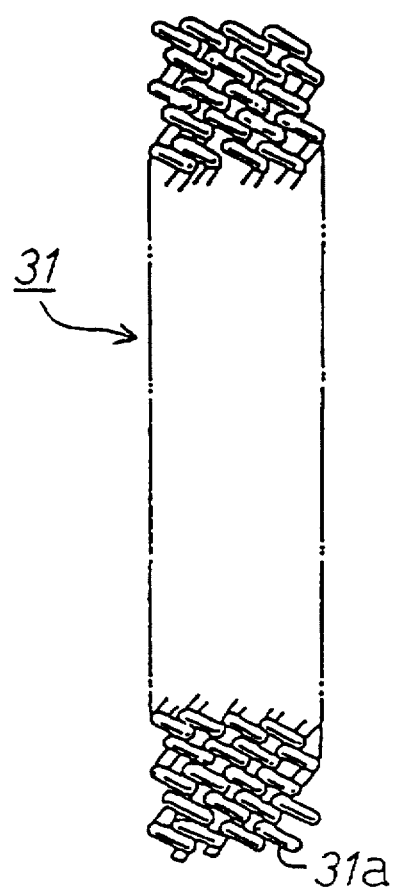
FIG. 7(A) is an illustration of a spiral wire mesh which is used for preparing a liquid permeable topsheet.
Figure 7B:
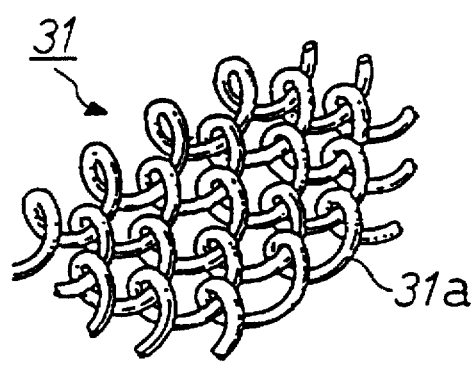
FIG. 7(B) is an enlarged view of the spiral wire mesh of FIG. 7(A).
Figure 8A:
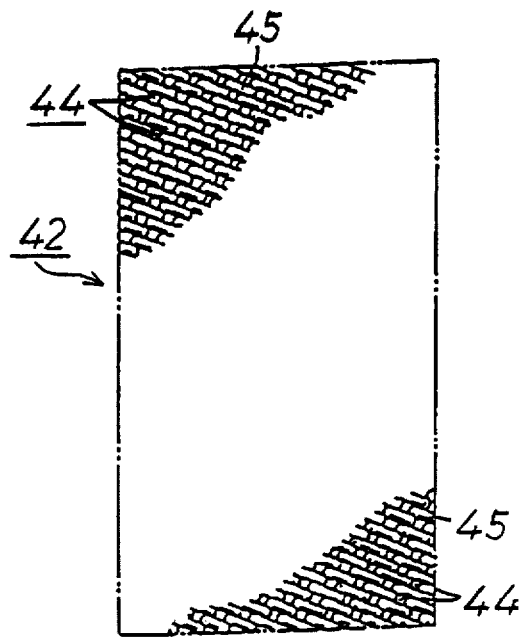
FIG. 8(A) is a schematic view illustrating a liquid permeable topsheet.
Figure 8B:
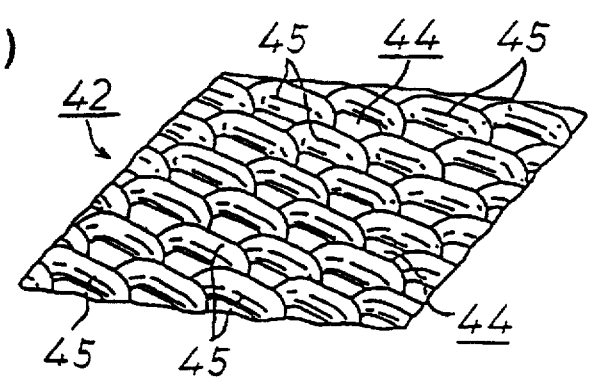
FIG. 8(B) is an enlarged view of the topsheet shown in FIG. 8(A)

A perforated film can be produced by, for example, the following process. A polyolefin, such as low-density polyethylene, is melt-extruded from a T-die to form a film on a spiral wire mesh 31 made of wires 31a as shown in FIGS. 7(A) and (B) The film on the mesh is then sucked to obtain a perforated film 42 having openings 44 as shown in FIG. 8(A). The perforated film 42 has a large number of bosses 45 having a curved surface and a large number of openings 44 among the bosses 45 as shown in FIGS. 8(B) and (C).

The backsheet 23 is not particularly limited as far as it is impermeable to liquid. Materials having moisture permeability and an underwear-like touch are preferred. A moisture permeable and liquid impermeable backsheet can be obtained by, for example, melt-extruding a thermoplastic resin containing an organic or inorganic filler into a film through a T-die or a circular die and uniaxially or biaxially stretching the extruded film.

The characteristics of the absorbent article according to the present invention consist in that the absorbent member 22 comprises at least an absorbent sheet 22A and a superabsorbent polymer 22B as shown in FIG. 5. The absorbent member 22 having such a structure is extremely thin so as to give a wearer a comfortable feel on use, and yet it exhibits high absorptivity and hardly causes leakage.

In more detail, the superabsorbent polymer 22B is included in the inside of the absorbent sheet 22A, i.e., interposed between upper and lower sides of the absorbent sheet 22A. It is preferable that the superabsorbent polymer 22B is included in the inside of the absorbent sheet 22A in such a manner that the back side of the absorbent sheet 22A contacts the superabsorbent polymer 22B. With this structure, liquid having passed through the topsheet 21 is quickly absorbed into the surface side of the absorbent sheet 22A and smoothly transferred to the back side of the absorbent sheet 22A. The liquid having reached the back side of the absorbent sheet 22A is diffused throughout the absorbent sheet 22A and then fixed into the superabsorbent polymer 22B.

The absorbent article of the present invention thus performs liquid absorption, permeation, diffusion, and retention functions extremely smoothly. As a result, the absorbent article is capable of fixing absorbed liquid very securely, causing neither liquid remaining on the surface of the topsheet 21 nor back-flow of absorbed liquid to the topsheet 21. Further, where the absorbent member 22 consists solely of the single absorbent sheet 22A and the superabsorbent polymer 22B, the absorbent article can be designed to have an extremely small thickness to give a satisfactory feel on use.

The superabsorbent polymer 22B is preferably such that can absorb and retain 20 or more times as much liquid as its own weight and is capable of gelation on absorption. The superabsorbent polymer 22B is not particularly limited in its shape and includes spheres, flakes and particles. Examples of such superabsorbent polymers are starch-acrylic acid (or a salt thereof) grafted polymers, saponified starch-acrylonitrile copolymers, crosslinked sodium carboxymethyl cellulose, and acrylic acid (or a salt thereof) polymers.

Figure 6:
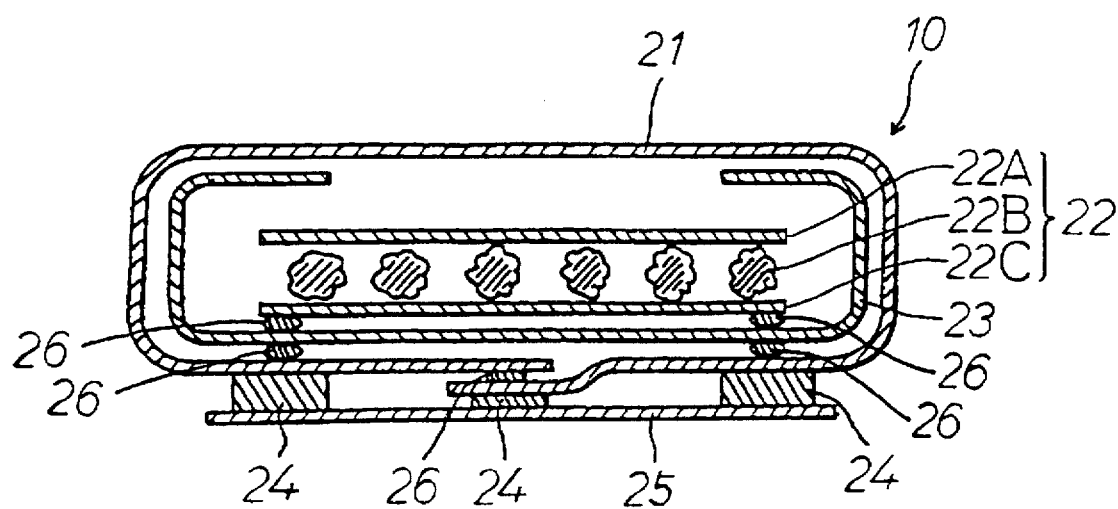
FIG. 6 is a schematic view illustrating the transverse section of a sanitary napkin as another embodiment of the absorbent article of the present invention, the view corresponding to FIG. 5.

Another type of sanitary napkins as another embodiment of the absorbent article of the present invention is described by referring to FIG. 6. While the particulars common to the embodiment of FIG. 5 are not described, the corresponding explanation given to FIG. 5 applies to FIG. 6 appropriately. The same reference numerals as used in FIG. 5 are used for the same members of FIG. 6.

In the sanitary napkin 10 shown in FIG. 6 as another embodiment of the absorbent article of the present invention, the absorbent member 22 is composed of a pair of the absorbent sheets 22A and 22C and the superabsorbent polymer 22B interposed between the absorbent sheets 22A and 22C. It is preferable that the absorbent sheet 22A contacts the superabsorbent polymer 22B on its back side, so does the absorbent sheet 22C. Still preferably, both the absorbent sheets 22A and 22C contact the superabsorbent polymer 22B on the back side thereof. Such a structure allows smooth performance of liquid absorption, permeation, diffusion, and retention functions.

While the absorbent articles of the present invention have been described by referring to the preferred embodiments thereof, the absorbent articles are not limited to these embodiments and can be used as other absorbent articles, such as disposable diapers, hygienic pads, medical pads, pads for incontinence, nursing breast pads, etc. as well as sanitary napkins.

EXAMPLES

The absorbent sheet of the present invention, the process for producing the same, and the absorbent article using the same will be illustrated in greater detail by way of Examples and Comparative Examples.

Processes for preparing bulky cellulose fibers and hydrophilic fine fibers or particles which can be used in the following Examples and Comparative Examples are shown below. Unless otherwise indicated, all the parts and percents are given by weight.

Preparation Example 1

Preparation of Cellulose Fibers

One hundred grams of mercerized pulp having an average fiber length of 2.35 mm, a degree of fiber roughness of 0.36 mg/m, and a degree of fiber roundness in the fiber cross section of 0.80 ("Porosanier-J", produced by ITT Rayonier Inc.) were dispersed in 1000 g of an aqueous solution containing 5% dimethylolhydroxyethyleneurea (crosslinking agent "Sumitex Resin NS-19" produced by Sumitomo Chemical Co., Ltd.) and 3% metal salt catalyst ("Sumitex Accelerator X-110" produced by Sumitomo Chemical Co., Ltd.) thereby to impregnate the mercerized pulp with the crosslinking agent.

The crosslinking agent aqueous solution was removed from the mercerized pulp until the amount of the crosslinking agent aqueous solution was reduced to 200% based on the mercerized pulp. The mercerized pulp was heated in an electric dryer at 135° C. for 10 minutes to crosslink the cellulose in the mercerized pulp to obtain crosslinked mercerized pulp. The resulting crosslinked mercerized pulp is designated cellulose fibers (A).

Preparation Example 2

Preparation of Cellulose Fibers

Crosslinked pulp was prepared in the same manner as in Preparation Example 1, except for using softwood kraft pulp having an average fiber length of 2.56 mm, a degree of fiber roughness of 0.35 mg/m and a degree of fiber roundness in the fiber cross section of 0.28 ("Indorayon" produced by PT Inti Indorayon Utama). The resulting mercerized crosslinked pulp is designated cellulose fibers (B).

Preparation Example 3

Preparation of Cellulose Fibers

Mercerized pulp having an average fiber length of 2.35 mm, a degree of fiber roughness of 0.36 mg/m, and a degree of fiber roundness in the fiber cross section of 0.80 ("Porosanier-J" produced by ITT Rayonier Inc.) was prepared. The resulting mercerized pulp is designated cellulose fibers (C).

Preparation Example 4

Preparation of Cellulose Fibers

Crosslinked pulp having an average fiber length of 2.38 mm, a degree of fiber roughness of 0.32 mg/m, and a degree of fiber roundness in the fiber cross section of 0.30 ("High Bulk Additive HBA-S" produced by Weyerhauser Paper Co.) was prepared. The resulting crosslinked pulp is designated cellulose fibers (D).

Preparation Example 5

Preparation of Cellulose Fibers

Softwood kraft pulp having an average fiber length of 2.56 mm, a degree of fiber roughness of 0.24 mg/m, and a degree of fiber roundness in the fiber cross section of 0.34 ("Harmac-R" produced by MacMillan Bloedel Ltd.) was prepared. The softwood kraft pulp is designated cellulose fibers (E). The cellulose fibers (E) are non-crosslinked fibers.

Preparation Example 6

Preparation of Cellulose Fibers

Softwood kraft pulp having an average fiber length of 2.56 mm, a degree of fiber roughness of 0.35 mg/m, and a degree of fiber roundness in the fiber cross section of 0.28 ("Indorayon" produced by PT Inti Indorayon Utama) was prepared. The resulting softwood kraft pulp is designated cellulose fibers (F). The cellulose fibers (F) are non-crosslinked fibers.

Preparation Example 7

Preparation of Cellulose Fibers

Crosslinked pulp was prepared in the same manner as in Preparation Example 1, except for using hardwood kraft pulp having an average fiber length of 0.75 mm, a degree of fiber roughness of 0.13 mg/m and a degree of fiber roundness in the fiber cross section of 0.35 ("Bahia Sul Cellulose SA" produced by Bahia Sul Co.) The resulting crosslinked pulp is designated cellulose fibers (G).

The average fiber length, the degree of roughness, and the degree of fiber roundness in the fiber cross section of cellulose fibers (A) to (G) were measured in accordance with the methods described below. The results obtained are shown in Table 1 below.

Measurement of Average Fiber Length and Degree of Fiber Roughness:

Measurement was made with a fiber roughness meter FS-200 manufactured by Kajaani Electronics Ltd. In order to measure the true weight of cellulose fibers, cellulose fibers are dried in a vacuum dryer at 100° C. for 1 hour to remove the water content.

Immediately thereafter, about 1 g of the cellulose fibers is weighed out to a precision of ±0.1 mg and completely disaggregated in 150 ml of water by means of a mixer attached to the fiber roughness meter. The suspension is diluted with water to make 5000 ml. A 50 ml aliquot of the diluted suspension is precisely measured out as a sample solution for measurement of fiber roughness. The average fiber length and the degree of fiber roughness are determined according to the operating procedure of the fiber roughness meter. The average fiber length is obtained from the following formula:

$$\text{Average fiber length} = \sum_{i=1}^{n} n_i l_i^2 / \sum_{i=1}^{n} n_i l_i$$

wherein $n_i$ is the number of fibers having fiber length $l_i$; and $l_i$ is a fiber length.

Measurement of Degree of Fiber Roundness in Fiber Cross Section:

The degree of fiber roundness in the fiber cross section of cellulose fibers is obtained as follows. A cellulose fiber is transversely sliced with care not to change the sectional area, and an electron micrograph of the section is taken. The micrograph is analyzed by an image analyzer ("Avio EXCEL" manufactured by Nippon Avionics Co., Ltd.) to obtain a degree of fiber roundness in the fiber cross section according to the following formula. Measurement is made on arbitrarily chosen 100 points to obtain the average. The degree of fiber roundness in the fiber cross section was obtained by averaging the measured values.

$$\text{Degree of fiber roundness in fiber cross section} = 4 \times \pi \times (\text{sectional area of a fiber})/(\text{circumference of the section of the fiber})^2$$

TABLE 1

| | Cellulose Fiber | | | | | | |
|---|---|---|---|---|---|---|---|
| | A | B | C | D | E | F | G |
| Average Fiber Length (mm) | 2.35 | 2.56 | 2.35 | 2.38 | 2.56 | 2.56 | 0.75 |
| Degree of Fiber Roughness (mg/m) | 0.36 | 0.35 | 0.36 | 0.32 | 0.24 | 0.35 | 0.13 |
| Degree of Fiber Roundness in Fiber Cross Section | 0.80 | 0.28 | 0.80 | 0.30 | 0.34 | 0.28 | 0.35 |
| Crosslinking | done | done | undone | done | undone | undone | done |

Preparation Example 8

Preparation of Hydrophilic Fine Fibers

Cellulose fine fibers having an average fiber length of 0.23 mm ("KC Flock W-50" produced by Sanyo-Kokusaku Pulp Co., Ltd.), designated hydrophilic fine fibers (A), were prepared. The hydrophilic fine fibers (A) are a product obtained by hydrolyzing refined pulp with an acid, washing with water, drying, and mechanically grinding the fibers into fine fibers.

Preparation Example 9

Preparation of Hydrophilic Fine Fibers

Cellulose fibers having an average fiber length of 0.12 mm ("KC Flock W-100" produced by Sanyo-Kokusaku Pulp Co., Ltd.), designated hydrophilic fine fibers (B), were prepared. The hydrophilic fine fibers (B) are a product obtained by hydrolyzing carefully selected pulp with an acid, washing with water, drying, and mechanically grinding the fibers into fine fibers.

Preparation Example 10

Preparation of Hydrophilic Fine Fibers

Magnesium silicate hydrate fine fibers having an average fiber length of 0.03 mm ("Eight Plus ML-30" produced by Mizusawa Kagaku Kogyo K.K.), designated hydrophilic fine fibers (C), were prepared.

Preparation Example 11

Preparation of Hydrophilic Fine Fibers

Hardwood kraft pulp having an average fiber length of 0.75 mm ("Bahia Sul Cellulose SA" produced by Bahia Sul Co.), designated hydrophilic fine fibers (D), were prepared.

Preparation Example 12

Preparation of Hydrophilic Fine Fibers

Softwood kraft pulp having an average fiber length of 2.34 mm ("Skeena Prime" produced by Skeena Cellulose Co.), designated hydrophilic fine fibers (E), were prepared.

Example 1

Preparation of Absorbent Sheet

In water were uniformly dispersed the cellulose fibers (A), the hydrophilic fine fibers (A), and polyvinyl alcohol fibers having a fineness of 1 denier and an average fiber length of 3 mm (thermally fusible bonding fibers "Fibribond" produced by Sansyo K.K., hereinafter referred to as PVA fibers) in a concentration of 0.16%, 0.03%, and 0.01%, respectively, to prepare a 0.2% slurry. The resulting slurry was spread on a paper making wire having an opening size of 90 μm (166 mesh) to form a paper layer. The paper layer was dehydrated in a suction box at a rate of 6 ml/(cm$^2$·sec), dried in a dryer, and subjected to 10% creping to obtain an absorbent sheet having a basis weight of 80 g/m$^2$. The resulting absorbent sheet contained 80 parts of the cellulose fibers (A), 15 parts of the hydrophilic fine fibers (A), and 5 parts of PVA fibers, based on 100 parts of the absorbent sheet.

Example 2

Preparation of Absorbent Sheet

An absorbent sheet having a basis weight of 80 g/m$^2$ was obtained in the same manner as in Example 1, except that the slurry was prepared by uniformly dispersing the cellulose fibers (B), the hydrophilic fine fibers (B), and the PVA fibers in water in a concentration of 0.16%, 0.034%, and 0.006%, respectively. The resulting absorbent sheet contained 80 parts of the. cellulose fibers (B), 17 parts of the hydrophilic fine fibers (B), and 3 parts of the PVA fibers.

Example 3

Preparation of Absorbent Sheet

An absorbent sheet having a basis weight of 80 g/m$^2$ was obtained in the same manner as in Example 1, except that the slurry was prepared by uniformly dispersing the cellulose fibers (D), the hydrophilic fine fibers (A), and polyethylene terephthalate fibers having a fineness of 1.1 denier and an average fiber length of 5 mm (thermally fusible bonding fibers "TMOTNSB" produced by Teijin Ltd., hereinafter referred to as PET fibers) in water in a concentration of 0.15%, 0.04%, and 0.01%, respectively. The resulting absorbent sheet contained 75 parts of the cellulose fibers (D), 20 parts of the hydrophilic fine fibers (A), and 5 parts of the PET fibers.

Example 4

Preparation of Absorbent Sheet

In water were uniformly dispersed the cellulose fibers (D), the hydrophilic fine fibers (C), and the PVA fibers in a concentration of 0.17%, 0.02%, and 0.01%, respectively, to prepare a slurry. The resulting slurry was spread on a paper making wire having an opening size of 26 μm (518 mesh) to form a paper layer. The paper layer was dehydrated in a suction box at a rate of 6 ml/(cm$^2$·sec), dried in a dryer, and subjected to 10% creping to obtain an absorbent sheet having a basis weight of 80 g/m². The resulting absorbent sheet contained 85 parts of the cellulose fibers (D), 10 parts of the hydrophilic fine fibers (C), and 5 parts of the PVA fibers, based on 100 parts of the absorbent sheet.

Example 5

Preparation of Absorbent Sheet

An absorbent sheet having a basis weight of 80 g/m² was obtained in the same manner as in Example 1, except that the slurry was prepared by uniformly dispersing the cellulose fibers (C), the hydrophilic fine fibers (A), and the PET fibers in water in a concentration of 0.16%, 0.03%, and 0.01%, respectively. The resulting absorbent sheet contained 80 parts of the cellulose fibers (C), 15 parts of the hydrophilic fine fibers (A), and 5 parts of the PET fibers, based on 100 parts of the absorbent sheet.

Comparative Example 1

Preparation of Absorbent Sheet

An absorbent sheet having a basis weight of 80 g/m² was obtained in the same manner as in Example 1, except for replacing the cellulose fibers (A) with the cellulose fibers (E).

Comparative Example 2

Preparation of Absorbent Sheet

An absorbent sheet having a basis weight of 80 g/m² was obtained in the same manner as in Example 2, except for replacing the cellulose fibers (B) with the cellulose fibers (G).

Comparative Example 3

Preparation of Absorbent Sheet

An absorbent sheet having a basis weight of 80 g/m² was obtained in the same manner as in Example 1, except that the slurry was prepared by uniformly dispersing the cellulose fibers (F), the hydrophilic fine fibers (D), and the PET fibers in water in a concentration of 0.16%, 0.03%, and 0.01%, respectively. The resulting absorbent sheet contained 80 parts of the cellulose fibers (F), 15 parts of the hydrophilic fine fibers (D), and 5 parts of the PET fibers, based on 100 parts of the absorbent sheet.

Comparative Example 4

Preparation of Absorbent Sheet

An absorbent sheet having a basis weight of 80 g/m² was obtained in the same manner as in Example 1, except that the slurry was prepared by uniformly dispersing the cellulose fibers (G), the hydrophilic fine fibers (E), and the PET fibers in water in a concentration of 0.16%, 0.03%, and 0.01%, respectively. The resulting absorbent sheet contained 80 parts of the cellulose fibers (G), 15 parts of the hydrophilic fine fibers (E), and 5 parts of the PET fibers, based on 100 parts of the absorbent sheet.

Comparative Example 5

Preparation of Absorbent Sheet

An absorbent sheet having a basis weight of 80 g/m² was obtained in the same manner as in Example 1, except that the slurry was prepared by uniformly dispersing the cellulose fibers (D), the hydrophilic fine fibers (E), and the PET fibers in water in a concentration of 0.08%, 0.04%, and 0.08%, respectively. The resulting absorbent sheet contained 40 parts of the cellulose fibers (D), 20 parts of the hydrophilic fine fibers (E), and 40 parts of the PET fibers, based on 100 parts of the absorbent sheet.

Comparative Example 6

Preparation of Absorbent Sheet

An absorbent sheet having a basis weight of 80 g/m² was obtained in the same manner as in Example 1, except that the slurry was prepared by uniformly dispersing the cellulose fibers (E) in water in a concentration of 0.2%. The resulting absorbent sheet consisted solely of the cellulose fibers (E).

Comparative Example 7

Preparation of Absorbent Sheet

An absorbent sheet having a basis weight of 80 g/m² was obtained in the same manner as in Example 1, except that the slurry was prepared by uniformly dispersing the hydrophilic fine fibers (D) in water in a concentration of 0.2%. The resulting absorbent sheet consisted solely of the hydrophilic fine fibers (D).

Each of the absorbent sheets prepared in Examples 1 to 5 and Comparative Examples 1 to 7 was tested according to the following methods. The results obtained are shown in Table 2 below.

Figure 9:
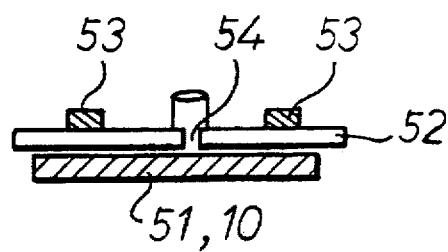
FIG. 9 is a schematic view illustrating a device for measuring the time of absorption.

Measurement of Absorbing Time:

As shown in FIG. 9, a 200 mm long and 75 mm wide absorbent sheet 51 was horizontally placed, and the acrylic plate 52 having a throughhole of 10 mm in diameter in the center thereof was placed on the absorbent sheet. Weights 53 were put thereon to apply a load of 5 g/cm² to the absorbent sheet. Six grams of defibrinated equine blood (produced by Nihon Biotec Kenkyusho K.K.) was poured through the hole, and the time required for the defibrinated equine blood was completely absorbed was measured. The measurement was made 5 times per sample, and an absorbing time was obtained by averaging the measured values.

Figure 10:
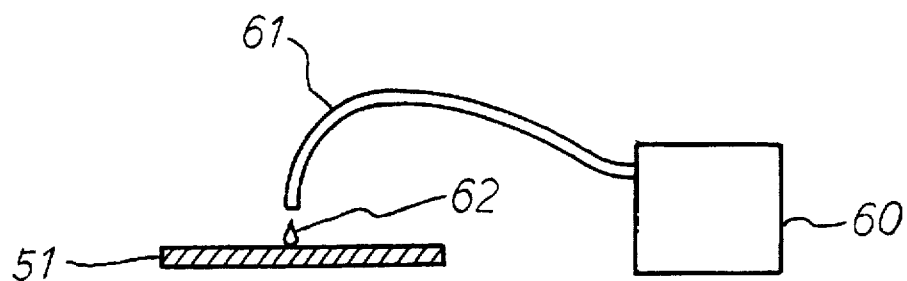
FIG. 10 is a schematic view illustrating a device for measuring the area of diffusion.
Figure 11:
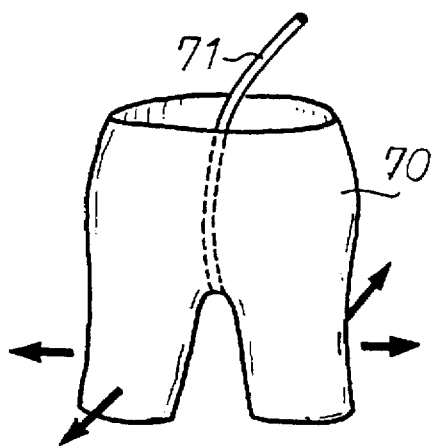
FIG. 11 illustrates a movable model of female hips and crotch.

Measurement of Diffusion Area:

As shown in FIG. 10, a 200 mm long and 75 mm wide absorbent sheet 51 was horizontally placed with its surface side up. One gram of physiological saline 62, tinted with 0.01% of Blue No. 1 for foodstuffs (produced by Tokyo Kasei Kogyo K.K.), was dropped on the absorbent sheet 51 at a rate of 1 g/10 sec from a microtube pump 60 through a tube 61 having a diameter of 2 mm. The tip of the tube 61 was about 10 mm above the absorbent sheet.

After about 1 minute from the injection of physiological saline, the diffusion area (cm²) in the surface side of the absorbent sheet was accurately traced and measured with an image analyzer.

The same procedure was repeated, while keeping the back side of the absorbent sheet 51 up, and the diffusion area (cm²) was accurately traced and measured with an image analyzer.

A ratio of the diffusion area in the back side to that in the surface side was obtained according to the following formula. The calculated value was rounded off to one decimal.

Diffusing area ratio=(diffusion area in back side)/(diffusion area in surface side)

Evaluation of Surface Condition After Liquid Absorption:

As shown in FIG. 10, a 200 mm long and 75 mm wide absorbent sheet 51 was horizontally placed with its surface side up. Three grams of the physiological saline 62 was dropped on the absorbent sheet 51 at a rate of 1 g/10 sec from the microtube pump 60 through the tube 61 having a diameter of 2 mm.

About 1 minute later from the dropping of physiological saline, the feel of dryness of the surface side was organoleptically evaluated.

The same procedure was repeated, while keeping the back side of the absorbent sheet 51 up.

The standard of evaluation is as follows.

Good
  The surface of the absorbent sheet feels dry with little physiological saline retained thereon.
Fair
  The surface of the absorbent sheet feels slightly dry with a little physiological saline retained thereon
Poor
  The surface of the absorbent sheet feels sticky with physiological saline considerably retained thereon.

side of the absorbent sheet 22A over an area of 195 mm length×70 mm width at a rate of 50 g/m². The absorbent sheet 22A was folded to envelop the superabsorbent polymer 22B in, to prepare the absorbent member 22 having a width of 75 mm with the surface side of the absorbent sheet 22A outward.

The absorbent member 22 was covered with polyethylene laminated paper (the backsheet 23), and the combination of the absorbent member 22 and the backsheet 23 was further enveloped with the topsheet 21. The topsheet 21, the absorbent member 22, and the backsheet 23 were bonded together with the adhesive 26.

Figure 8C:
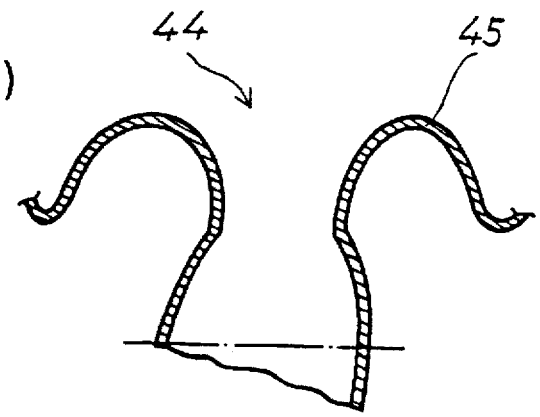
FIG. 8(C) is an enlarged cross sectional view of the topsheet shown in FIG. 8(A).

The topsheet 21 used above was a perforated film shown in FIGS. 8(A) to (C), which was prepared by melt-extruding low-density polyethylene from a T-die to form a film on a spiral wire mesh shown in FIGS. 7(A) and (B) and sucking the film.

Finally, three adhesive bands 24 were provided on the bottom of the sanitary napkin 10 in the longitudinal direction. The adhesive bands 24 were protected by the release paper 25.

TABLE 2

| | Composition of Absorbent Sheet (part) | | | | Diffusion Area (cm²) | | Surface Side/ Back Side | Surface Condition |
|---|---|---|---|---|---|---|---|---|
| | Hydrophilic Cellulose Fibers | Thermally Fusible Fine Fibers | Absorbing Bonding Fibers | Time (sec) | Surface Side | Back Side | Diffusion Area Ratio | After Absorption |
| Examples | | | | | | | | |
| 1 | A 80 | A 15 | PVA 5 | 22 | 6.5 | 33.5 | 5.2 | Good |
| 2 | B 80 | B 17 | PVA 3 | 31 | 12.5 | 38.1 | 3.0 | Good |
| 3 | D 75 | A 20 | PET 5 | 36 | 15.1 | 35.6 | 2.4 | Fair to Good |
| 4 | D 85 | C 10 | PVA 5 | 35 | 14.5 | 32.3 | 2.2 | Fair to Good |
| 5 | C 80 | A 15 | PET 5 | 43 | 18.1 | 36.5 | 2.0 | Fair to Good |
| Comparative Examples | | | | | | | | |
| 1 | E 80 | A 15 | PVA 5 | 325 | 33.5 | 34.2 | 1.0 | Poor |
| 2 | G 80 | B 17 | PVA 3 | 431 | 39.5 | 40.3 | 1.0 | Poor |
| 3 | F 80 | D 15 | PET 5 | 385 | 38.3 | 38.9 | 1.0 | Poor |
| 4 | G 80 | E 15 | PET 5 | 285 | 35.1 | 33.9 | 1.0 | Poor |
| 5 | D 40 | E 20 | PET 40 | 523 | 33.1 | 32.0 | 1.0 | Poor |
| 6 | E 100 | — | — | 318 | 35.1 | 33.9 | 1.0 | Poor |
| 7 | — | D 100 | — | 495 | 39.1 | 38.7 | 1.0 | Poor |

Example 6

Preparation of Absorbent Article

The sanitary napkin 10 shown in FIG. 5 was produced. The absorbent sheet obtained in Example 1 (195 mm long, 160 mm wide) was used as the absorbent sheet 22A. The superabsorbent polymer 22B ("Polymer Q" produced by Kao Corp.) was spread substantially uniformly on the back

Examples 7 to 10 and Comparative Examples 8 to 14

Sanitary napkins were produced in the same manner as in Example 6, except for replacing the absorbent sheet obtained in Example 1 with each of the absorbent sheets obtained in Examples 2 to 5 and Comparative Examples 1 to 7.

The sanitary napkins prepared in Examples 6 to 10 and Comparative Examples 8 to 14 were tested according to the following test methods to evaluate an absorbing time, and a back-flow in a moving mode and leakage (number of leaks). The results obtained are shown in Table 3 below.

Measurement of Absorbing Time and Back-flow in Moving Mode:

A device for measuring the rate of absorption of an absorbent sheet as shown in FIG. 9 was used. The sanitary napkin 10 was placed horizontally in place of the absorbent sheet 51. The acrylic plate 52 having an inlet 54 having a diameter of 10 mm was placed on the napkin, and weights 53 were put thereon to apply a load of 5 g/cm$^2$ to the sanitary napkin 10. Six grams of defibrinated equine blood (produced by Nihon Biotest Kenkyusho K.K.) were poured through the inlet 54, and the time required for the blood to be absorbed completely was measured.

Figure 12:
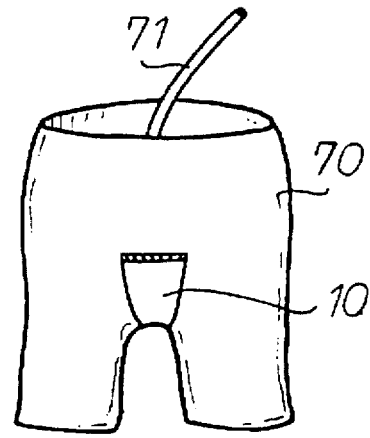
FIG. 12 illustrates the movable model of FIG. 11 with a sanitary napkin applied to the crotch.

After the complete absorption, the sanitary napkin was left to stand for 20 minutes. Then, 10 sheets of paper having a basis weight of 30 g/m$^2$ (196 mm long and 75 mm wide) were placed on the upper side of the sanitary napkin (the side to be in contact with the body). The sanitary napkin with paper on was applied to a movable model 70 of female hips and crotch as shown in FIG. 12. After fitting panties to the model 70, the model was made to take a walking movement at a rate of 100 steps/min (corresponding to a walking speed of 50 m/min).

After the walking movement, the sanitary napkin 10 and 10 sheets of paper were removed, and the weight of defibrinated equine blood absorbed into the paper was measured as a back-flow (g) in a moving mode.

The test was conducted 10 times for each sample, and each of the absorbing time and the back-flow in a moving mode was calculated by averaging the measured values thereof.

Leak Test (Number of Leaks):

The sanitary napkin obtained in Examples 6 to 10 and Comparative Examples 8 to 14 was applied to the movable model 70 of female hips and crotch as shown in FIG. 12, and panties were fitted thereon. The model 70 was made to take a walking movement at a rate of 100 steps/min (corresponding to a walking speed of 50 m/min).

While keeping the model 70 in a moving mode, 3 g of defibrinated equine blood was poured into the sanitary napkin, and the walking movement was continued for 10 minutes at the same walking speed (3 g-absorption). Another 3 g of defibrinated equine blood was again poured, followed by walking at the same speed for another 10 minutes (6 g-absorption). A still another 3 g of defibrinated equine blood was poured, followed by walking at the same speed for 10 minutes more (9 g-absorption). The test was conducted 10 times per sample, and the samples having a leak at each time point of 3 g-absorption, 6 g-absorption, and 9 g-absorption were counted.

TABLE 3

| | Absorbing Time (sec) | Moving Mode Back-flow (g) | Number of Leaking Samples | | |
|---|---|---|---|---|---|
| | | | 3 g | 6 g | 9 g |
| Examples | | | | | |
| 6 | 10 | 0.1 | 0 | 0 | 0 |
| 7 | 15 | 0.1 | 0 | 0 | 0 |
| 8 | 18 | 0.2 | 0 | 0 | 2 |
| 9 | 18 | 0.2 | 0 | 0 | 3 |

TABLE 3-continued

| | Absorbing Time (sec) | Moving Mode Back-flow (g) | Number of Leaking Samples | | |
|---|---|---|---|---|---|
| | | | 3 g | 6 g | 9 g |
| 10 | 22 | 0.3 | 0 | 0 | 4 |
| Comparative Examples | | | | | |
| 8 | 83 | 0.8 | 0 | 5 | 10 |
| 9 | 121 | 1.0 | 0 | 7 | 10 |
| 10 | 105 | 0.9 | 0 | 6 | 10 |
| 11 | 75 | 0.7 | 0 | 3 | 10 |
| 12 | 158 | 1.3 | 3 | 10 | 10 |
| 13 | 88 | 0.8 | 0 | 5 | 10 |
| 14 | 135 | 0.9 | 0 | 5 | 10 |

As is apparent from the results in Table 3, the absorbent articles according to the present invention exhibit excellent performance as having a high rate of liquid absorption, a reduced amount of a back-flow, and causing little leakage in spite of the very simple structure thereof. This is because the absorbent sheet used in the absorbent articles of the present invention has a liquid absorption and diffusion gradient in its single structure and therefore quickly absorbs liquid, smoothly transfer the absorbed liquid therethrough, and sufficiently diffuses the liquid in the back side thereof.

Many other variations and modifications of the invention will be apparent to those skilled in the art without departing from the spirit and scope of the invention. The above-described embodiments are, therefore, intended to be merely exemplary, and all such variations and modifications are intended to be included within the scope of the invention as defined in the appended claims.

What is claimed is:

1. An absorbent sheet containing bulky cellulose fibers and hydrophilic fine fibers or hydrophilic fine particles, characterized in that:

the proportion of the hydrophilic fine fibers or the hydrophilic fine particles is higher in a back side of the absorbent sheet than in a surface side;

the bulky cellulose fibers have an average fiber length of 1 to 20 mm and a degree of fiber roughness of 0.3 mg/m or more;

the hydrophilic fine fibers have an average fiber length of 0.02 to 0.5 mm; and the hydrophilic fine particles have an average particle diameter of 0.02 to 0.5 mm.

2. The absorbent sheet according to claim 1, wherein the absorbent sheet comprises 50 to 97 parts by weight of the bulky cellulose fibers, and 3 to 50 parts by weight of the hydrophilic fine fibers or the hydrophilic fine particles, based on 100 parts by weight of the absorbent sheet.

3. The absorbent sheet according to claim 1, wherein the absorbent sheet further comprises thermally fusible bonding fibers;

the absorbent sheet comprises 70 to 95 parts by weight of the bulky cellulose fibers and 5 to 30 parts by weight of the hydrophilic fine fibers or the hydrophilic fine particles, and 2 to 30 parts by weight of the thermally fusible bonding fibers, based on 100 parts by weight of the absorbent sheet; and the basis weight of the absorbent sheet is 10 to 200 g/m$^2$.

4. The absorbent sheet according to claim 1, wherein the bulky cellulose fibers have a degree of fiber roundness in the fiber cross section of 0.5 to 1.

5. The absorbent sheet according to claim 1, wherein the hydrophilic fine fibers are cellulose fibers, and the hydrophilic fine particles are cellulose particles.

6. The absorbent sheet according to claim 1, wherein the ratio of a diffusion area of the side having a higher proportion of the hydrophilic fine fibers or particles to that of the side having a lower proportion of the hydrophilic fine fibers or particles is 1.2 or more, the diffusion area being measured by allowing the respective sides to absorb 1 g of physiological saline.

7. The absorbent sheet according to claim 1, wherein the bulky cellulose fibers have an average fiber length of 2 to 5 mm.

8. The absorbent sheet according to claim 7, wherein the bulky cellulose fibers are crosslinked pulp fibers.

9. The absorbent sheet according to claim 7, wherein the bulky cellulose fibers have a degree of fiber roundness in the fiber cross section of 0.5 to 1.

10. The absorbent sheet according to claim 1, wherein the bulky cellulose fibers are crosslinked pulp fibers.

11. The absorbent sheet according to claim 10, wherein the bulky cellulose fibers have a degree of fiber roundness in the fiber cross section of 0.5 to 1.

12. An absorbent article comprising a liquid permeable topsheet, a liquid impermeable backsheet and a liquid retentive absorbent member interposed between the topsheet and the backsheet, characterized in that:

the absorbent member contains one or two absorbent sheets and a superabsorbent polymer;

the one or two absorbent sheets containing bulky cellulose fibers and hydrophilic fine fibers or hydrophilic fine particles;

the proportion of the hydrophilic fine fibers or the hydrophilic fine particles is higher in a back side of the one or two absorbent sheets than in a surface side;

the bulky cellulose fibers have an average fiber length of 1 to 20 mm;

the hydrophilic fine fibers have an average fiber length of 0.02 to 0.5 mm; and the hydrophilic fine particles have an average particle diameter of 0.02 to 0.5 mm.

13. The absorbent article according to claim 12, wherein the absorbent member comprises the one or two absorbent sheets surrounding the superabsorbent polymer.

14. The absorbent article according to claim 12, wherein the absorbent member comprises two absorbent sheets containing superabsorbent polymer dispersed therebetween.

* * * * *